US009867904B2

(12) United States Patent
Comer et al.

(10) Patent No.: US 9,867,904 B2
(45) Date of Patent: *Jan. 16, 2018

(54) DRIED AND IRRADIATED SKIN EQUIVALENTS FOR READY USE

(71) Applicant: Stratatech Corporation, Madison, WI (US)

(72) Inventors: Allen R. Comer, Madison, WI (US); B. Lynn Allen-Hoffmann, Madison, WI (US); Barry Steiglitz, Madison, WI (US)

(73) Assignee: Stratatech Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/377,323

(22) Filed: Dec. 13, 2016

(65) Prior Publication Data

US 2017/0087276 A1  Mar. 30, 2017

Related U.S. Application Data

(60) Continuation of application No. 14/669,095, filed on Mar. 26, 2015, now Pat. No. 9,526,811, which is a continuation of application No. 14/220,320, filed on Mar. 20, 2014, now Pat. No. 8,992,997, which is a continuation of application No. 14/054,445, filed on Oct. 15, 2013, now Pat. No. 8,685,463, which is a division of application No. 12/612,284, filed on Nov. 4, 2009, now Pat. No. 8,580,314.

(60) Provisional application No. 61/111,153, filed on Nov. 4, 2008.

(51) Int. Cl.
| | |
|---|---|
| A61L 27/60 | (2006.01) |
| A61L 27/36 | (2006.01) |
| A61L 27/38 | (2006.01) |
| A61F 2/10 | (2006.01) |
| A61L 27/54 | (2006.01) |

(52) U.S. Cl.
CPC ......... *A61L 27/3691* (2013.01); *A61F 2/105* (2013.01); *A61L 27/3813* (2013.01); *A61L 27/54* (2013.01); *A61L 27/60* (2013.01); *A61L 2430/40* (2013.01)

(58) Field of Classification Search
None
See application file for complete search history.

(56) References Cited

U.S. PATENT DOCUMENTS

| | | |
|---|---|---|
| 4,485,096 A | 11/1984 | Bell |
| 5,536,656 A | 7/1996 | Kemp |
| 5,693,332 A | 12/1997 | Hansbrough |
| 5,968,546 A | 10/1999 | Baur |
| 5,989,837 A | 11/1999 | Allen-Hoffmann |
| 6,039,760 A | 3/2000 | Eisenberg |
| 6,585,969 B1 | 7/2003 | Van Bossuyt |
| 6,846,675 B2 | 1/2005 | Conrad |
| 6,974,697 B2 | 12/2005 | Comer |
| 7,407,805 B2 | 8/2008 | Comer |
| 7,462,448 B2 | 12/2008 | Allen-Hoffmann |
| 7,498,167 B2 | 3/2009 | Comer |
| 7,501,238 B2 | 3/2009 | Comer |
| 7,541,188 B2 | 6/2009 | Conrad |
| 7,674,291 B2 | 3/2010 | Centanni |
| 7,807,148 B2 | 10/2010 | Comer |
| 7,888,496 B2 | 2/2011 | Allen-Hoffmann |
| 7,955,790 B2 | 6/2011 | Comer |
| 2002/0192197 A1 | 12/2002 | Kuri-Harcuch et al. |
| 2005/0079578 A1 | 4/2005 | Centanni et al. |
| 2005/0186185 A1 | 8/2005 | Conrad |
| 2006/0141627 A1 | 6/2006 | Comer |
| 2006/0222635 A1 | 10/2006 | Centanni |
| 2006/0257383 A1 | 11/2006 | Allen-Hoffmann |
| 2006/0258001 A1 | 11/2006 | Allen-Hoffmann |
| 2006/0292126 A1 | 12/2006 | Hunziker et al. |
| 2008/0145344 A1 | 6/2008 | Desphande et al. |
| 2008/0226720 A1 | 9/2008 | Kemp et al. |
| 2009/0145087 A1 | 6/2009 | Allen-Hoffmann |
| 2009/0169528 A1 | 7/2009 | Comer |
| 2010/0099576 A1 | 4/2010 | Comer |
| 2010/0119495 A1 | 5/2010 | Centanni |
| 2010/0119615 A1 | 5/2010 | Comer |
| 2010/0330046 A1 | 12/2010 | Comer |
| 2011/0059057 A1 | 3/2011 | Comer |

FOREIGN PATENT DOCUMENTS

| | | |
|---|---|---|
| CA | 2758178 | 2/2005 |
| CN | 1800372 A | 7/2006 |
| JP | 9-173362 | 7/1997 |

(Continued)

OTHER PUBLICATIONS

Allen-Hoffmann, et al., J. Invest. Dermatol., 114(3): 444-455 (2000).
Asbill, et al., Pharm. Research 17(9): 1092-97 (2000).
Auger, et al., In Vitro Cell. Dev. Biol.—Animal 36(2):96-103 (2000).
Baden, In Vitro Cell. Dev. Biol. 23(3):205-213 (1987).
Boucamp, et al., J. Cell. Biol. 106(3):761-771 (1988).
Cancio, L.C., et al., Burn support for Operation Iraqi Freedom and related operations, 2003 to 2004, J Burn Care Rehabil, 2005, 26(2): p. 151-61.
Meana, et al., Burns 24(7):621-30 (1998).

(Continued)

*Primary Examiner* — Robert Yamasaki

(57) ABSTRACT

The present invention relates generally to systems and methods for preparing, storing, shipping and using skin equivalents made by organotypic culture. In particular, the present invention relates to systems and methods for producing, transporting, storing and using skin equivalents produced by organotypic culture at reduced temperatures, preferably from 2-8 degrees Celsius to ambient temperature. The methods include sterile packaging of the grafts so that the sterility and integrity of the package is maintained until the time of use for grafting purposes.

11 Claims, 8 Drawing Sheets

(56) References Cited

FOREIGN PATENT DOCUMENTS

| | | |
|---|---|---|
| WO | 93/10217 | 5/1993 |
| WO | 96/14738 | 5/1996 |
| WO | 01/54619 | 8/2001 |
| WO | 02/070729 | 9/2002 |
| WO | 03/093418 | 11/2003 |
| WO | 2004/013606 | 2/2004 |
| WO | 2004/110372 | 12/2004 |
| WO | 2005/012492 | 2/2005 |
| WO | 2006/055931 | 5/2006 |
| WO | 2006/094070 | 9/2006 |
| WO | 2006/101834 | 9/2006 |
| WO | 2009/065005 | 5/2009 |
| WO | 2010/053948 | 5/2010 |
| WO | 2010/135655 | 11/2010 |

OTHER PUBLICATIONS

Milner, S.M. and M.R. Ortega, Reduced antimicrobial peptide expression in human burn wounds. Burns, 1999, 25(5): p. 411-13.
Rosales, Int Wound J., 2004. 1(3): p. 201-6.
English translation of CN first Office Action dated Nov. 28, 2012 from related CN Patent Application No. 200980154244.2.
English translation of first Office Action dated Oct. 29, 2013 from related JP Patent Application No. 2011-535637.
P.R. Mohd Adha, et al., "Usage of Allogeneic Single Layered Tissue Engineered Skin Enhance Wound Treatment in Sheep," Med J Malaysia, Jul. 2008, 63 Suppl A, p. 30-1.
Singh, Rita, et al., "Microbiological Safety and Clinical Efficacy of Radiation Sterilized Amniotic Membranes for Treatment of Second-Degree Burns," Burns 33 (2007) pp. 505-510.
Pedraza, Jorge Morales, et al., "The impact of the International Atomic Energy Agency (IAEA) program on radiation and tissue banking in Asia and the Pacific and the Latin American regions," Cell Tissue Bank (2008).

DRIED AND IRRADIATED SKIN EQUIVALENTS FOR READY USE

CROSS REFERENCE TO RELATED APPLICATIONS

This application is a continuation of U.S. patent application Ser. No. 14/669,095, filed Mar. 26, 2015, which is a continuation of U.S. patent application Ser. No. 14/220,320, filed Mar. 20, 2014, now U.S. Pat. No. 8,992,997, which is a continuation of U.S. patent application Ser. No. 14/054,445, filed Oct. 15, 2013, now U.S. Pat. No. 8,685,463, which is a divisional of U.S. patent application Ser. No. 12/612,284, now U.S. Pat. No. 8,580,314, filed Nov. 4, 2009, which claims the benefit of U.S. Provisional Patent Application No. 61/111,153, filed Nov. 4, 2008, the contents of all of which are incorporated by reference herein in their entireties.

STATEMENT REGARDING FEDERALLY SPONSORED RESEARCH OR DEVELOPMENT

This invention was made with government support under W81XWH-07-C-0063 awarded by the U.S. Army Medical Research and Material Command. The government has certain rights in the invention.

FIELD OF THE INVENTION

The present invention relates generally to systems and methods for long-term storage at refrigerated or ambient temperature of skin equivalents made by organotypic culture.

BACKGROUND

The emerging field of tissue engineering (TE) is poised to make enormous progress in the treatment of organ disease and dysfunction in the coming decade. In 2001, there were 23 cell-based therapeutics approved for market in the United States (U.S.) and Europe, of which nine were skin substitutes or grafts, and 100 more products were in development. (De Bree, Genomics-based Drug Data Report and Regenerative Therapy (1) 2:77-96 (2001)). In 2007, nearly 100 companies were involved in developing engineered tissues, cell-based therapeutics, or related technologies (Applied Data Research, February 2007). Overall the industry had an annual growth rate of 16% from 1995-2001. The "structural" industry segment (e.g., skin, bone, cartilage) showed 85% growth from 1998-2001. In 2004, the U.S. market for tissue-engineered skin replacements/substitutes and active wound repair modulators was valued at approximately $195 million. Sales are expected to increase at a compound annual rate of 9.5%, reaching approximately $481 million in the year 2014 (MedTech Insight, Windhover Information, September 2005). The total U.S. market for advanced wound care technologies was worth more than $2.3 billion in 2005. This has been projected to grow at an average annual growth rate of 12.3% over a five year period to reach $4.6 billion in 2011 (BCC Research, PHM011E, January 2007). The global wound care market is estimated to be worth US$ 7.2 billion in 2006 and comprises two sectors, traditional and advanced (Espicom Business Intelligence, 2007). Traditional wound care products consist mainly of low technology gauze-based dressings such as woven and non-woven sponges, conforming bandages and non-adherent bandages. The advanced wound care segment (US$ 4.1 billion global) is the fastest growing area with double-digit growth of 10% per year (Espicom Business Intelligence, 2007).

Although a multitude of revolutionary and economically important applications for engineered tissues and organs exist in the human health arena, the full economic potential of the industry is far from realized. At present, only one of the publicly-held tissue engineering companies worldwide has shown a profit despite global investment in these technologies exceeding $3.5 billion. (Lysaght and Reyes, Tissue Engineering 7(5):485-93 (2001)).

A major impediment to the acceptance of engineered tissues by medical practitioners, healthcare providers, and second party payers is the lack of a means to effectively and efficiently preserve and store engineered tissues. The nature of living cells and tissue products makes them impractical for long-term storage. Current engineered tissues must often be stored and shipped under carefully controlled conditions to maintain viability and function. Typically, engineered tissue products take weeks or months to produce but must be used within hours or days after manufacture. As a result, TE companies must continually operate with their production facilities at top capacity and absorb the costs of unsold product which must be discarded. These inventory losses, on top of already costly manufacturing process, have forced prices to impractical levels. As one specific example, APLIGRAF requires about four weeks to manufacture, is usable for only ten days and must be maintained between 20 and 23° C. until used. As another example, EPICEL is transported by a nurse from Genzyme Biosurgery's production facility in Cambridge, Mass. to the point of use in a portable incubator and is used immediately upon arrival. Such constraints represent significant challenges to developing convenient and cost-effective products.

Cryopreservation has been explored as a solution to the storage problem, but it is known to induce tissue damage through ice formation, chilling injury, and osmotic imbalance. Besides APLIGRAF, the only other approved living skin equivalent, ORCEL, is currently in clinical trials as a frozen product but has the drawback that it must be maintained at temperatures below −100° C. prior to use. This requires specialized product delivery and storage conditions, including the use of dangerous goods during transport, and use of liquid nitrogen for storage, which is expensive, dangerous, and not readily available in rural clinics and field hospitals. Moreover, delivering a frozen product requires special training on the part of the end user to successfully thaw the tissue prior to use.

Accordingly, what is needed in the art are improved methods of preparing engineered tissues and cells for storage under conditions that are routinely available at the point of use. As all clinical facilities have refrigerated storage, development of a skin equivalent that can be stored for prolonged periods in a standard refrigerator would greatly improve the availability and clinical utility of these products. Development of a skin equivalent that can be stored for prolonged periods at ambient temperatures would further increase the availability of such products for immediate use on the battlefield or in a variety of first response situations.

SUMMARY OF THE INVENTION

The present invention relates generally to systems and methods for long-term storage at refrigerated or ambient temperature of skin equivalents made by organotypic culture. In some embodiments, the present invention provides methods of preserving an organotypically cultured skin equivalent for use as a wound dressing comprising: providing said organotypically cultured skin equivalent and a package; treating said skin equivalent to render cells in the skin equivalent non-viable; and packaging said skin equivalent to provide a packaged skin equivalent. The present invention is not limited to any particular method of treating the skin equivalent to render the cells making up the skin equivalent non-viable. In some embodiments, the treating step comprises irradiating said packaged skin equivalent so that said skin equivalent is rendered sterile and non-viable. In some embodiments, the irradiating is performed with gamma irradiation. In some embodiments, the treating step comprises drying said skin equivalent under conditions such that cells in said skin equivalent are rendered non-viable. The present invention is not limited to any particular method of drying. In some embodiments, the drying is performed by a method selected from the group consisting of vacuum drying and freeze drying. The present invention is not limited to any particular order of steps, unless otherwise indicated. In some embodiments, the treating occurs before packaging. In some embodiments, the treating occurs after packaging. In some embodiments, the treating comprises drying said skin equivalent under conditions such that cells making up said skin equivalent are rendered non-viable and irradiating said skin equivalent under conditions such that said skin equivalent is rendered sterile. In some embodiments, the drying step occurs before said packaging and said irradiation step occurs after said packaging step.

The present invention is not limited to the use of any particular skin equivalent. In some embodiments, the organotypically cultured skin equivalent comprises NIKS cells. In some embodiments, the NIKS cells comprise an exogenous nucleic acid sequence encoding an exogenous polypeptide. In some embodiments, more than one exogenous polypeptide is expressed by the cells making up this skin equivalent. The present invention is not limited to the use of any particular exogenous polypeptide. In some embodiments, the exogenous polypeptide is an antimicrobial polypeptide. In some embodiments, the antimicrobial polypeptide is selected from the group consisting of human beta-defensin 1, human beta-defensin 2, human beta-defensin 3, and cathelicidin. In some embodiments, the antimicrobial polypeptide is provided by the skin equivalent in a quantity of from 1 to 1000 ng of antimicrobial polypeptide per milliliter of a surface extraction solution, in some preferred embodiments, the antimicrobial polypeptide is provided by the skin equivalent in a quantity of from 1 to 1000 ng of antimicrobial polypeptide per milliliter of a surface extraction solution. In some embodiments, the skin equivalent is dried to a final mass of less than 75%, 50%, 25% or preferably 15% of that of a wet or non-dried skin equivalent. In some embodiments, the skin equivalent, after rehydration, has an initial DPM value of from about 20 DPM to about 300 DPM, preferably from about 70 to about 140 DPM, and a DPM change value of from about 5 DPM to about 400 DPM, preferably from about 10 DPM to about 220 DPM. In some embodiments, the skin equivalent, after rehydration, has a tensile strength of from about 0.1 to about 5.0 MPa, preferably from about 0.4 to about 1.8 MPa. In some embodiments, the package is heat sealable.

In some embodiments, the present invention provides a packaged human skin equivalent produced by the foregoing methods. In some embodiments, the present invention provides a packaged, sterile human skin equivalent produced by the foregoing methods.

In some embodiments, the present invention provides compositions comprising an isolated, non-viable, in vitro human skin equivalent. In some embodiments, the skin equivalent is packaged. In some embodiments, the skin equivalent is sterile. In some embodiments, the sterile skin equivalent is irradiated. In some embodiments, the skin equivalent is dried. In some embodiments, the skin equivalent has a mass of less than 50% of the mass of a wet skin equivalent. In some embodiments, the skin equivalent comprises NIKS cells. In some embodiments, the NIKS cells comprise an exogenous nucleic acid sequence encoding an exogenous polypeptide. In some embodiments, more than one exogenous polypeptide is expressed by the cells making up the skin equivalent. The present invention is not limited to the use of any particular exogenous polypeptide. In some embodiments, the exogenous polypeptide is an antimicrobial polypeptide. In some embodiments, the antimicrobial polypeptide is selected from the group consisting of human beta-defensin 1, human beta-defensin 2, human beta-defensin 3, and cathelicidin. In some embodiments, the antimicrobial polypeptide is provided by the skin equivalent in a quantity of from 1 to 1000 ng of antimicrobial polypeptide per milliliter of a surface extraction solution, in some preferred embodiments, the antimicrobial polypeptide is provided by the skin equivalent in a quantity of from 1 to 1000 ng of antimicrobial polypeptide per milliliter of a surface extraction solution. In some embodiments, the skin equivalent is dried to a final mass of less than 75%, 50%, 25% or preferably 15% of that of a wet or non-dried skin equivalent. In some embodiments, the skin equivalent, after rehydration, has an initial DPM value of from about 20 DPM to about 300 DPM, preferably from about 70 to about 140 DPM, and a DPM change value of from about 5 DPM to about 400 DPM, preferably from about 10 DPM to about 220 DPM. In some embodiments, the skin equivalent, after rehydration, has a tensile strength of from about 0.1 to about 5.0 MPa, preferably from about 0.4 to about 1.8 MPa.

In some embodiments, the present invention provides methods for treating a subject comprising providing a skin equivalent composition as described above and applying said skin equivalent to a wound under conditions such that said skin equivalent contacts said wound. In some embodiments, the skin equivalent is applied to said wound temporarily.

In some embodiments, the present invention provides kits comprising a package containing the skin equivalent composition described above. In some embodiments, the skin equivalent has a shelf life of from about one month to about six months.

In some embodiments, the present invention provides compositions comprising a nonviable, isolated, in vitro organotypically cultured skin equivalent having a mass of less than 50% of the mass of a wet skin equivalent. In some embodiments, the compositions comprise at least one exogenous antimicrobial polypeptide expressed by cells integral to said skin equivalent.

In some embodiments, the present invention provides for the use of the foregoing compositions to treat a subject. In some embodiments, the present invention provides for the use of the foregoing compositions to treat a wound on a subject.

DEFINITIONS

Figure 1:
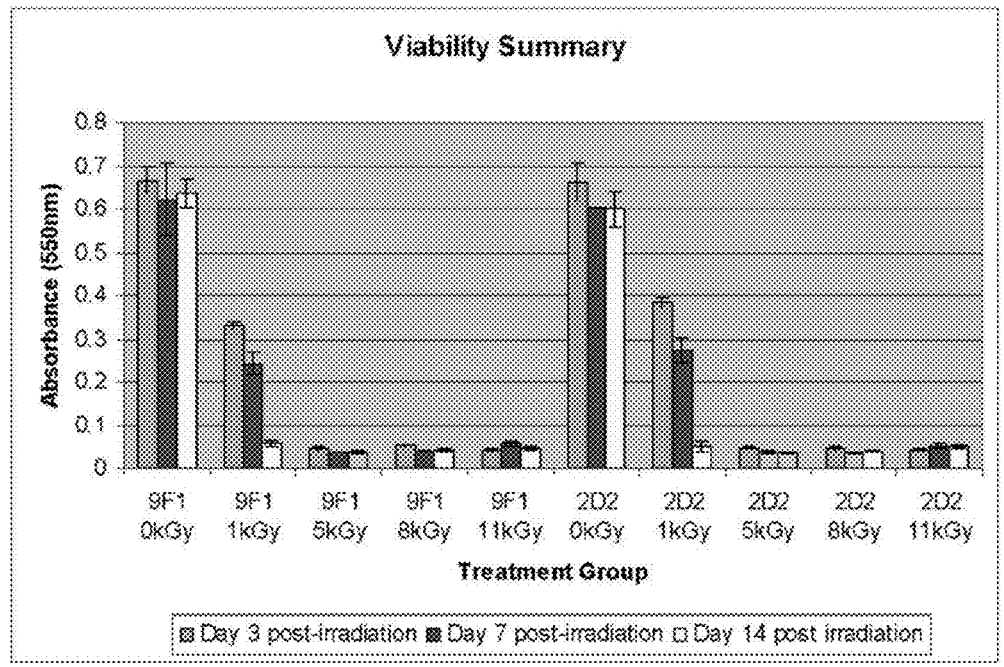
FIG. 1. Viability of tissues post-irradiation. 9F1 and 2D2 tissues were irradiated, and punch biopsies were harvested at 3, 7, or 14 days post-irradiation and analyzed for viability using MTT assay. Data represent means+/−the standard deviation measured from at least three independent biopsy samples in each treatment group.

As used herein, the terms "skin equivalent", "human skin equivalent", "human skin substitute", and "organotypic cultures" are used interchangeably to refer to an in vitro derived culture of keratinocytes that has stratified into squamous epithelia. Typically, the skin equivalents are produced by organotypic culture and include a dermal layer in addition to a keratinocyte layer.

As used herein, the term "wet skin equivalent" refers to a skin equivalent in organotypic culture or immediately removed from organotypic culture.

As used herein, the term "non-viable" refers to cells that are not living as determined by an assay such as an MTT assay.

As used herein, the term "sterile" refers to a skin equivalent that is essentially or completely free of microbial or fungal contamination.

As used herein, the term "dried" refers to a composition from which moisture has been removed. A "dried skin equivalent" is a skin equivalent from which moisture has been removed so that the dried skin equivalent has a lower moisture content that a skin equivalent that is wet, or immediately removed from organotypic culture. Comparison of the mass of the dried skin equivalent to a wet skin equivalent is used as a measure of the extent of drying and reflects the amount of moisture removed from the skin equivalent during the drying process.

As used herein, the term "NIKS cells" refers to cells having the characteristics of the cells deposited as cell line ATCC CRL-1219.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The term "gene" refers to a nucleic acid (e.g., DNA) sequence that comprises coding sequences necessary for the production of a polypeptide or precursor (e.g., KGF-2). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "recombinant DNA molecule" refers to a DNA molecule that is comprised of segments of DNA joined together by means of molecular biological techniques.

As used herein, the term "purified" or "to purify" refers to the removal of contaminants from a sample.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "antimicrobial polypeptide" refers to generally short polypeptides, from 5 to 100 amino acids in length, the exhibit antimicrobial activity. Examples of antimicrobial polypeptides include, but are not limited to, human beta-defensins 1, 2, and 3 and cathelicidin. The sequences of a wide variety of antimicrobial polypeptides within the scope of the invention are known and available, including those identified in WO 05/012,492, incorporated by reference herein in its entirety.

DETAILED DESCRIPTION

The present invention relates generally to systems and methods for preparing, shipping and storing skin equivalents made by organotypic culture. In particular, the present invention relates to methods for drying or irradiating human skin equivalents to eliminate the viability of the skin equivalent so that it can be stored for prolonged periods and transported under standard conditions for use in the field, or on-site use, as opposed to use in a hospital.

Medical planning was a critical part of Operation Iraqi Freedom and included predictive models of the expected number of burn casualties (Barillo, D. J., et al., Tracking the daily availability of burn beds for national emergencies. J Burn Care Rehabil, 2005. 26(2): p. 174-82). In these models the casualty estimates exceeded the capacity of the only Department of Defense burn center. The Department of Defense in conjunction with the American Burn Association developed a mass casualty plan based on the current practices and technology available for burn care. In the first Gulf War the opposing force was known to have used chemical weapons including sulfur mustard. In the current Iraqi and Afghanistan conflicts, the number of field burns has reached new levels. Cutaneous thermal and chemical vesicant (blistering) burns, as well as the procedures of deroofing and debridement commonly used to treat these injuries, lead to open wounds susceptible to infection by bacterial pathogens.

Unfortunately, in the last 25 years there has been a significant lack of innovative, life saving technologies developed for the treatment of cutaneous burn or vesicant wounds. The need for innovations in this area was emphasized by the Oct. 25-28, 2006 conference entitled "State of the Science of Burn Research" sponsored by the National Institute of General Medical Sciences. Gamma-irradiated human cadaver skin is stable at ambient temperature and has been successfully used in the treatment of skin defects (Rosales, M. A., M. Bruntz, and D. G. Armstrong, Gamma-irradiated human skin allograft: a potential treatment modality for lower extremity ulcers. Int Wound J, 2004. 1(3): p. 201-6; Cancio, L. C., et al., Burn support for Operation Iraqi Freedom and related operations, 2003 to 2004. J Burn Care Rehabil, 2005. 26(2): p. 151-61). However, such products are not indicated for use in wounds that show evidence of infection. Cutaneous wounds, such as those resulting from vesicant exposure and thermal injuries, provide an ideal environment for bacterial growth and the complications stemming from wound sepsis. Moreover, the increasing frequency of multi-drug resistant clinical isolates of organisms such as *Acinetobacter baumannii*, *Pseudomonas aeruginosa*, and methicillin-resistant *Staphylococcus aureus* (MRSA) underscores the need for novel approaches to supplement the current antimicrobial treatment regimes used in cutaneous wound therapy (Milner, S. M. and M. R. Ortega, Reduced antimicrobial peptide expression in human burn wounds. Burns, 1999. 25(5): p. 411-3).

In some embodiments, the present invention provides a field-ready, tissue-engineered dried or irradiated antimicrobial skin equivalent for treatment of vesicant, thermal, and traumatic cutaneous injuries. The dried or irradiated skin equivalent is designed for long term storage at ambient temperatures and maximal versatility and safety to patients with vesicant, thermal, or traumatic injury to external epithelia. In preferred embodiments, the dried or irradiated skin equivalents are engineered to deliver the broad spectrum human host defense peptides β-defensin-3 (hBD-3) or cathelicidin (hCAP18/LL-37) to the wound bed.

Accordingly, in some embodiments, the present invention provides a dried or irradiated human skin equivalent comprising non-viable cells. In some embodiments, the skin equivalent has been engineered to express and provide exogenous antimicrobial polypeptides, preferably human β-defensin-1, 2 or 3 or cathelicidin (hCAP18/LL37). In some embodiments, the non-viable skin equivalents are applied to wounds. In some embodiments, the non-viable human skin equivalents are applied temporarily to wounds. In some embodiments, the non-viable human skin equivalents are removed and replaced with additional non-viable human skin equivalents providing the same antimicrobial polypeptide. In other embodiments, the non-viable skin equivalents are removed and replaced with additional non-viable skin equivalents providing a different antimicrobial polypeptide. In other embodiments non-viable human skin equivalents are removed prior to application of a viable skin equivalent or a permanent skin graft on the wound (e.g., burn wound).

In preferred embodiments, the skin equivalents of the present invention are engineered to express an exogenous antimicrobial polypeptide. The present invention is not limited to the use of any particular antimicrobial polypeptide. In preferred embodiments, the antimicrobial polypeptide is human β-defensin-1, human β-defensin-2, human (β-defensin-3, or cathelicidin (hCAP-18/LL37) or variant. In some preferred embodiments, nucleic acid constructs or vectors encoding the antimicrobial polypeptide are introduced into the keratinocytes (e.g., NIKS cells) and the transfected keratinocytes are used to make the skin equivalent by organotypic culture techniques. Preferred embodiments for the production of skin equivalents expressing exogenous polypeptides, as well as additional wild-type and variant antimicrobial polypeptides, are provided in co-pending application Ser. No. 10/909,119, the entire contents of which are incorporated herein by reference.

A) Skin Equivalents Produced by Organotypic Culture

The present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of these cell lines can be cultured or genetically modified in order to produce a cell line capable of expressing or co-expressing the desired protein(s). In particularly preferred embodiments, NIKS cells are utilized. The discovery of a novel human keratinocyte cell line (near-diploid immortalized keratinocytes or NIKS) provides an opportunity to genetically engineer human keratinocytes with non-viral vectors. A unique advantage of the NIKS cells is that they are a consistent source of genetically-uniform, pathogen-free human keratinocytes. For this reason, they are useful for the application of genetic engineering and genomic gene expression approaches to provide skin equivalent cultures with enhanced properties over currently available technologies and skin tissue products. The NIKS keratinocyte cell line, identified and characterized at the University of Wisconsin, is nontumorigenic, exhibits a stable karyotype, and exhibits normal growth and differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, the immortalized NIKS cells will continue to proliferate in monolayer culture indefinitely. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies which exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescencing population were originally designated BC-1-Ep/Spontaneous Line and are now termed NIKS. The NIKS cell line has been screened for the presence of proviral DNA sequences for HIV-1, HIV-2, EBV, CMV, HTLV-1, HTLV-2, HBV, HCV, B-19 parvovirus, HPV-16, SV40, HHV-6, HHV-7, HPV-18 and HPV-31 using either PCR or Southern analysis. None of these viruses were detected.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. The karyotype of the NIKS cells has been shown to be stable to at least passage 54.

The DNA fingerprints for the NIKS cell line and the BC-1-Ep keratinocytes are identical at all twelve loci analyzed demonstrating that the NIKS cells arose from the parental BC-1-Ep population. The odds of the NIKS cell line having the parental BC-1-Ep DNA fingerprint by random chance is $4 \times 10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium were investigated. NIKS cells remained as single cells after 4 weeks in either agar- or methylcellulose-containing medium. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both submerged culture and organotypic culture. Techniques for organotypic culture are described in detail in the examples. In particularly preferred embodiments, the organotypically cultured skin equivalents of the present invention comprise a dermal equivalent formed from collagen or a similar material and fibroblasts. The keratinocytes, for example NIKS cells or a combination of NIKS cells and cells from a patient are seeded onto the dermal equivalent and form an epidermal layer characterized by squamous differentiation following the organotypic culture process.

For cells in submerged culture, the formation cornified envelopes was monitored as a marker of squamous differentiation. In cultured human keratinocytes, early stages of cornified envelope assembly result in the formation of an immature structure composed of involucrin, cystatin-α and other proteins, which represent the innermost third of the mature cornified envelope. Less than 2% of the keratinocytes from the adherent BC-1-Ep cells or the NIKS cell line produce cornified envelopes. This finding is consistent with previous studies demonstrating that actively growing, sub-confluent keratinocytes produce less than 5% cornified envelopes. To determine whether the NIKS cell line is capable of producing cornified envelopes when induced to differentiate, the cells were removed from adherent culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS keratinocytes produced as many as and usually more cornified envelopes than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in submerged culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper epidermal layers and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed.

To observe more detailed characteristics of the parental (passage 5) and NIKS (passage 38) organotypic cultures and to confirm the histological observations, samples were analyzed using electron microscopy. Parental cells and the immortalized NIKS human keratinocyte cell line were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted.

Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the porous support. These findings are consistent with earlier ultrastructural findings using human foreskin keratinocytes cultured on a fibroblast-containing porous support. Analysis at both the light and electron microscopic levels demonstrate that the NIKS cell line in organotypic culture can stratify, differentiate, and form structures such as desmosomes, basal lamina, and hemidesmosomes found in normal human epidermis.

B) Drying or Irradiation of Skin Equivalents

In preferred embodiments, the skin equivalents produced as described in Example 1 are irradiated and/or dried to provide a non-viable skin equivalent. In some embodiments, the skin equivalents are dried to eliminate cell viability. In some embodiments, the skin equivalents are irradiated, for example, gamma irradiated. In some embodiments, the skin equivalents are dosed with from about 0.5 kGy to about 25 kGy gamma radiation. In some embodiments, the skin equivalents are dosed from about 0.5 to about 12 kGy of radiation, more preferably from about 1 kGy to about 5 kGy gamma irradiation. In any event, the amount of radiation delivered to the skin equivalent is preferably enough to cause the cells contained in the skin equivalent to be non-viable as assayed by an MTT viability assay or other appropriate viability assays. In further preferred embodiments, the skin equivalents are dried under vacuum or freeze dried. In some embodiments, the skin equivalents are dried before irradiation. In some preferred embodiments, the skin equivalents are packaged in a sterile package prior to drying or irradiation. In further preferred embodiments, the skin equivalents are packaged with a sterile fabric such as gauze to permit storage, transport, and ease of use by the end user. In other embodiments, the dried or irradiated skin equivalents maintain the ability to release endogenous polypeptides to the surface of a wound after being contacted with a wound. In further embodiments, the dried or irradiated skin equivalents maintain the ability to release exogenous polypeptides to the wound after being contacted with the wound environment. In further embodiments, the skin equivalents are refrigerated prior to use, while in other embodiments, the skin equivalents are stored at ambient temperatures prior to use.

It will be recognized that the extent to which the skin equivalent has been dried can be determined by comparing the mass of the dried skin equivalent to the mass of a skin equivalent that has not been dried (a wet skin equivalent), i.e., a skin equivalent that has just been removed from organotypic culture. In some embodiments, the skin equivalent is dried to a final mass of less than 75%, 50%, 25% or preferably 15% of that of the wet skin equivalent. In some embodiments, the dried skin equivalents of the present invention have a mass of less than 75%, 50%, 25% or preferably 15% of that of a wet or non-dried skin equivalent. In some embodiments, the dried skin equivalents are rehydrated prior to application to a subject. In some embodiments, the rehydrated skin equivalents have a tensile strength of from 0.1 to 5.0 MPa, preferably from about 0.4 to about 1.8 MPa. In some embodiments, the rehydrated skin equivalents have an initial DPM value of from about 20 DPM to about 300 DPM, preferably from about 70 to about 140 DPM, and a DPM change value of from about 5 DPM to about 400 DPM, preferably from about 10 DPM to about 220 DPM.

In some embodiments, the dried and/or irradiated skin equivalents are utilized for delivery of a peptide or protein of interest to a subject, and in some preferred embodiments to a wound bed on a subject. Skin equivalents that express exogenous peptides and proteins have been previously described by the inventors, see, e.g., WO 05/012492, incorporated herein by reference in its entirety. In some embodiments, the skin equivalents are engineered to express one or antimicrobial polypeptides. In some embodiments, the antimicrobial polypeptide is cathelicidin, human beta-defensin 1, human beta-defensin 2, or human beta-defensin 3, or combinations thereof. In preferred embodiments, the peptide or polypeptide is exogenous, i.e., encoded and expressed by an exogenous gene construct engineered into the keratinocytes utilized to make the skin equivalent. The amount of peptide or polypeptide delivered by the skin equivalent can be determined by applying an aqueous solution to the skin equivalent and measuring the amount of peptide or polypeptide that is delivered into the solution. In some embodiments, the polypeptide is provided in a quantity of from 1 to 1000 ng of antimicrobial polypeptide per milliliter of a extraction solution. In some embodiments, the polypeptide is provided in a quantity of from 10 to 500 ng of antimicrobial polypeptide per milliliter of an extraction solution.

C) Therapeutic Uses

It is contemplated that the non-viable skin equivalents of the present invention may be used therapeutically. In some embodiments, the dried or irradiated skin is used in wound closure and burn treatment applications. The use of autografts and allografts for the treatment of burns and wound closure is described in Myers et al., A. J. Surg. 170(1):75-83 (1995) and U.S. Pat. Nos. 5,693,332; 5,658, 331; and 6,039,760, each of which is incorporated herein by reference. In some embodiments, the skin equivalents may be used in conjunction with dermal replacements such as DERMAGRAFT or INTEGRA. Accordingly, the present invention provides methods for wound closure, including wounds caused by burns, comprising providing a skin equivalent and a patient suffering from a wound and treating the patient with the skin equivalent under conditions such that the wound is closed.

In some embodiments, the skin equivalents are utilized to treat chronic skin wounds. Chronic skin wounds (e.g., venous ulcers, diabetic ulcers, pressure ulcers) are a serious problem. The healing of such a wound often takes well over a year of treatment. Treatment options currently include dressings and debridement (use of chemicals or surgery to clear away necrotic tissue), and/or antibiotics in the case of infection. These treatment options take extended periods of time and high amounts of patient compliance. As such, a therapy that can increase a practitioner's success in healing chronic wounds and accelerate the rate of wound healing would meet an unmet need in the field. Accordingly, the present invention contemplates treatment of skin wounds with skin equivalents comprising the cells of the present invention (e.g., NIKS cells). In some embodiments, skin equivalents are topically applied to wounds. In other embodiments, skin equivalents comprising NIKS cells are used for engraftment on partial thickness wounds. In other embodiments, skin equivalents comprising NIKS cells are used for engraftment on full thickness wounds. In other embodiments, skin equivalents comprising NIKS cells are used to treat numerous types of internal wounds, including, but not limited to, internal wounds of the mucous membranes that line the gastrointestinal tract, ulcerative colitis, and inflammation of mucous membranes that may be caused by cancer therapies. In still other embodiments, skin equivalents comprising NIKS cells expressing host defense peptides are used as a temporary or permanent wound dressing.

In still further embodiments, the cells are engineered to provide additional therapeutic agents to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, small interfering RNA (siRNA) micro RNA (miRNA), and antisense RNA. In preferred embodiments, the agents are host defense peptides such as human beta-defensin 1, 2, or 3 or cathelicidin, see, e.g., U.S. patent application Ser. No. 10/909,119, incorporated herein by reference in its entirety. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathesis) in which the graft serves as wild-type tissue. It is contemplated that delivery of the therapeutic agent corrects the defect. In some embodiments, the cells are transfected with a DNA construct encoding a therapeutic agent (e.g., insulin, clotting factor IX, erythropoietin, etc) and the transfected cells are administered to the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue-specific, and keratinocyte-specific promoters. In some embodiments, the nucleic acid encoding the therapeutic agent is introduced directly into the keratinocytes (i.e., by electroporation, calcium phosphate co-precipitation, or liposome transfection). In other preferred embodiments, the nucleic acid encoding the therapeutic agent is provided as a vector and the vector is introduced into the keratinocytes by methods known in the art. In some embodiments, the vector is an episomal vector such as a replicating plasmid. In other embodiments, the vector integrates into the genome of the keratinocytes. Examples of integrating vectors include, but are not limited to, retroviral vectors, adeno-associated virus vectors, non-replicating plasmid vectors and transposon vectors.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); mM (millimolar); µM (micromolar); N (Normal); mol (moles); mmol (millimoles); µmol (micromoles); nmol (nanomoles); g (grams); mg (milligrams); µg (micrograms); ng (nanograms); l or L (liters); ml or mL (milliliters); µl or µL (microliters); cm (centimeters); mm (millimeters); µ(micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin); CFU (colony forming units); kGy (kiloGray); PVDF (polyvinylidine fluoride); BCA (bicinchoninic acid); SDS-PAGE (sodium dodecyl sulfate polyacrylamide gel electrophoresis).

Example 1

This example describes a method for the production of skin equivalents.

Media.

The organotypic culture process uses three different culture media, all based on the formulation of SMB medium described in U.S. Pat. No. 7,407,805, with the exception that cholera toxin is omitted from all media. FM01 is used to propagate the normal human dermal fibroblasts (NHDFs) for use in skin equivalent dermal equivalent layers. FM01 has the same formulation as SMB except that it contains Fetal Clone II serum (2% final) and lacks cholera toxin. KM01 is used to grow NIKS keratinocytes and has the same composition as SMB except that it contains 2.5% fetal clone II, and additional epidermal growth factor (EGF) is added to a final concentration of 5 ng/ml. SM01 is used during the epidermal stratification phase of skin equivalent production and is identical to SMB except for the omission of cholera toxin.

Dermal Equivalent Preparation.

On day 0, frozen NHDF cells are thawed and plated. The cells are fed FM01 the next day (day 1) to remove residual cryoprotectant and again on day 3. On day 4, they are harvested for use in the dermal equivalent. To prepare the dermal equivalent, Type I rat-tail collagen is first diluted to 3 mg/ml in 0.03N acetic acid and chilled on ice. A mixture of concentrated Ham's F12 medium (8.7× normal strength and buffered with HEPES at pH 7.5) is mixed with fetal clone II. These two solutions are 11.3 and 9.6% of the final solution volume. 1N NaOH is added to the medium mixture (2.4% of final solution). The diluted collagen is then added (74.7%) to the mixture. A 2% volume of suspended fibroblasts ($2.78 \times 10^6$/ml) is added to the mixture. 9 ml of the final dermal equivalent mixture is poured into each 75 mm TRANSWELL insert (Corning Costar). After a 50-70 minute gel formation period, the Transwell inserts are transferred to the surface of a stainless steel mesh in a 150 mm culture dish. 80 ml of FM01 is placed in the 150 mm dish outside the TRANSWELL insert and 10 ml is placed on top of the dermal equivalent. The dermal equivalents are placed in 37° C., 5% $CO_2$, 90% relative humidity incubator for 4-5 days prior to use in the organotypic cultures.

NIKS Growth and Seeding.

NIKS cells are thawed and plated at a density of approximately $5 \times 10^5$ cells per 100 mm dish. NIKS culture can be performed in the presence or absence of murine feeder cells. On day 1, the NIKS cells are fed fresh KM01 to remove residual cryoprotectant. The NIKS cells are fed again on day 3. On day 4, the NIKS cells are harvested from the initial p100 cultures and seeded into 225 $cm^2$ culture flasks at a density of $1.2 \times 10^6$ per flask. The NIKS cultures are fed fresh medium on Days 7 and 8. On day 9, the NIKS cells are harvested, counted, and resuspended in SM01. $2.27 \times 10^4$ NIKS cells/$cm^2$ are seeded onto the surface of the dermal equivalents. The dishes are cultures are fed and lifted to the air-medium interface. Cultures are transferred to a controlled humidity incubator set to 75% where they remain for the rest of their growth. Cultures are fed SM01 on days 14, 18, 22, 25, 28, and 30.

Example 2

Determination of the Lethal Dose of Gamma Radiation Required to Produce Nonviable, Sterile Skin Equivalent Tissue The production schedule for development of irradiated skin equivalents was based on the 28-day production process previously established for engineered human skin tissue products. 9F1 and 2D2 tissues, which had been engineered for enhanced expression of the host defense peptides hBD-3 and hCAP18/LL-37, respectively, were produced using aseptic procedures. Tissues were transferred onto nutrient gel chambers and sealed prior to packaging and transport. Gamma irradiation was performed by Sterigenics, Inc. using the ExCell high precision gamma irradiator, at its Charlotte, N.C. facility. Tissues received one of five radiation doses: 0 kGy, 1 kGy, 5 kGy, 8 kGy, or 11 kGy. These doses were chosen based on previous evaluation of similar doses on allograft tissues. After irradiation, tissues were refrigerated prior to analysis at the times indicated below.

Upon return of processed samples to Stratatech, it was found that some tissues stored on nutrient gels were detached from their underlying support membranes, resulting in folding and wrinkling of tissues. This phenomenon was observed in both irradiated and nonirradiated tissues. Shipping procedures were subsequently developed that solve this problem. See Examples below.

Sterility Testing:

Punch biopsies were obtained from 9F1 and 2D2 tissues that had been subjected to gamma irradiation at doses ranging from 0 to 11 kGy. Samples from tissues stored for 3 days post-irradiation were inoculated into trypticase soy broth or fluid thioglycolate media. Cultures were incubated for 14 days under conditions defined for sterility testing by the US Pharmacopeia. After 14 days, cultures were visually examined for microbial growth. No microbial growth was observed for any of the analyzed tissues, demonstrating the tissues remained sterile throughout handling, irradiation, and transport.

Viability Testing by MTT Viability Assay:

Biopsies were obtained from control or gamma irradiated 9F1 and 2D2 tissues at 3 days, 7 days, or 14 days after irradiation treatment and cell viability was measured by MTT viability assay. Briefly, the MTT substrate, 3-(4,5-dimethylthiazolyl-2-yl)-2,5-diphenyl tetrazolium bromide, is converted to MTT formazan product by cellular dehydrogenases in viable cells. The colored product is then extracted into isopropanol and read at 550 nm. Viability was measured in four independent tissue batches, and representative results are shown in FIG. 1. The viability of unirradiated tissues did not change significantly during the storage period. Tissues treated with 1 kGy radiation had residual enzymatic activity at 3 days post-irradiation that continued to decrease at 7 and 14 days post-irradiation. However, tissues treated with 5, 8, or 11 kGy doses demonstrated minimal residual activity at all timepoints and remained low throughout the course of the 14-day storage period. By 14 days after irradiation, the metabolic activity of tissues irradiated with 1 kGy was reduced to the same low level seen with higher radiation doses.

Figure 2:
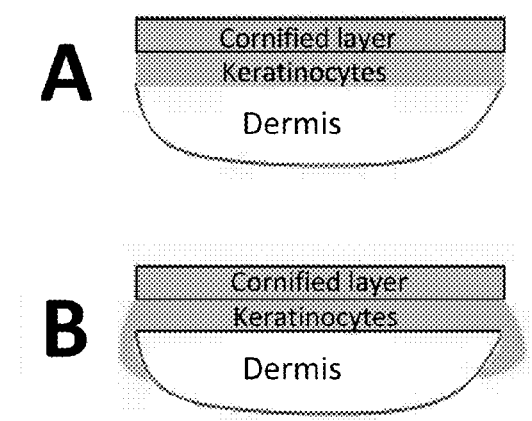
FIG. 2. Keratinocyte viability/migration assay (A). Explants which exhibited no keratinocyte outgrowth were scored negative for viable keratinocytes. (B). Samples in which keratinocytes had migrated around the edge of the dermis were scored positive for viable keratinocytes.

Viability Determination by Keratinocyte Migration Assay:

Biopsy explant cultures were established from control tissues or irradiated tissues to determine if keratinocytes were inactivated by radiation treatments. Punch biopsies obtained from tissues at 3 days post irradiation were transferred to growth media, cultured for 48 hours, and processed for histological staining using hematoxylin/eosin and digital microscopy. Images were obtained to assess tissue architecture and scored as positive or negative for keratinocyte migration out from wound edges created by biopsy punches according to the schematic in FIG. 2. Cell migration was evident in nonirradiated 9F1 and 2D2 tissues but was absent from all tissues subjected to gamma irradiation.

Figure 3:
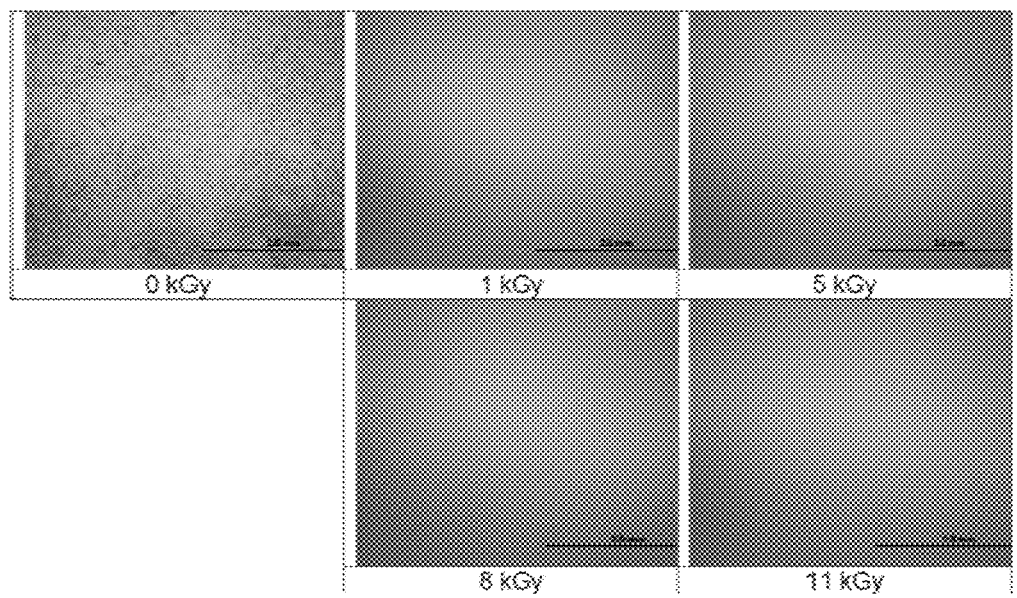
FIG. 3. Fibroblast outgrowth assay. Biopsies from control and irradiated 9F1 tissues were treated with collagenase, and isolated cells were cultured for six days prior to staining with 1% methylene blue to visualize colonies of cells.

Fibroblast Outgrowth Assay:

Biopsies were obtained from control and irradiated tissues at 7 days post-irradiation, and were treated with bacterial collagenase to release fibroblasts. Cells liberated from these tissues were transferred to culture plates, allowed to grow for six days in culture media, and visualized by methylene blue staining. Fibroblast cell outgrowth was scored as positive or negative based on the presence or absence of stained blue cells, respectively. Images of fibroblast cultures isolated from non-irradiated or irradiated tissues are shown in FIG. 3. Cell outgrowth was observed from control tissues receiving no radiation, but was absent from preparations derived from irradiated tissues.

From the above studies, it was determined that product sterility was maintained throughout production and processing of tissues. Treatment of skin equivalent tissues with radiation doses of 1 kGy yielded nonviable tissue using two independent assays of viability. Doses of 5 kGy or higher resulted in nonviable tissue as assessed by all three methods.

Example 3

Evaluation of the Structural Properties of Gamma-Irradiated Skin Equivalent Tissue The structural properties of irradiated tissues after 3 days of refrigerated storage were evaluated by histological staining with hematoxylin and eosin and visualized by light microscopy. Histological staining verified that irradiated tissues retain normal tissue organization and gross morphology. All cellular layers, including dermis, basal and spinous keratinocyte layers, and stratum corneum, were identifiable in nonirradiated control and irradiated tissues, though some tissue damage was apparent at higher radiation doses, visualized as gaps between the dermal and epidermal compartments. As a result, 1 kGy and 5 kGy dose levels were identified as the most promising for use in subsequent studies.

Example 4

Evaluation of the Biochemical Properties, Including the In Vitro Antimicrobial Activity, of Gamma-Irradiated Skin Equivalent Tissue Gamma radiation stimulates dose-dependent damage to proteins both directly and indirectly. Direct damage is initiated through ionization, while indirect damage involves hydrolysis of water molecules and oxidative modification or crosslinking of macromolecules. As a result, tissue protein may exhibit increased degradation and reduced solubility upon irradiation. Since the product under development is expected to function through provision of elevated levels of host defense peptides, it was necessary to determine protein accessibility and biological activity after irradiation. Analysis of irradiated tissues included soluble and total protein analysis, immunoblot analysis, and antimicrobial activity assays.

Figure 4:
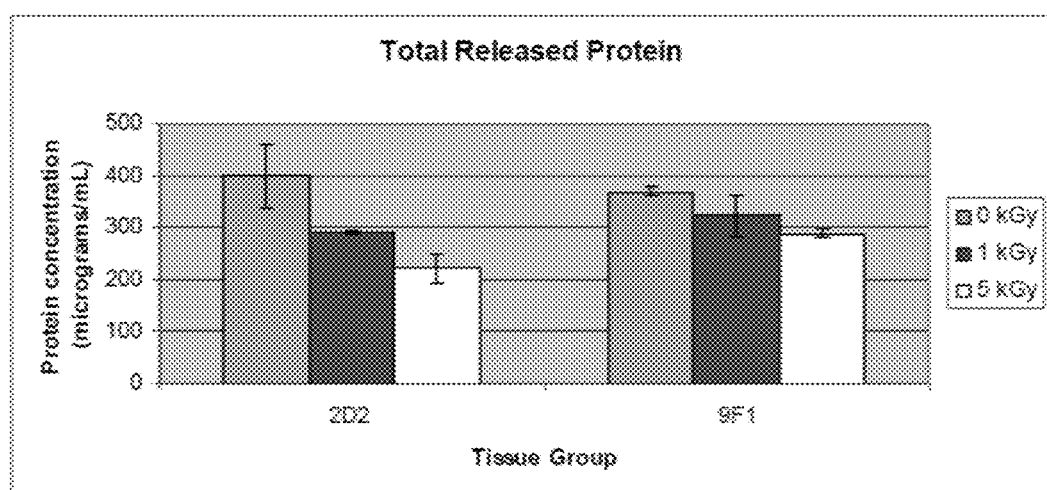
FIG. 4. Protein released from irradiated 2D2 and 9F1 tissues. Human skin substitute tissues were irradiated at a dose of 0, 1, or 5 kGy. Proteins were extracted in water from punch biopsies harvested at 3 days post-irradiation and quantified by BCA assay. Data represent mean values+/−the standard deviation from four measurements.

Soluble and Total Protein Analysis:

Punch biopsies were obtained from non-irradiated and irradiated 2D2 and 9F1 skin tissues and submerged in 0.2 mL sterile water. Biopsy samples were incubated at 37° C. for 72 hr to extract protein, supernatants were collected, and total protein quantified by BCA assay. As shown in FIG. 4, total protein eluted into the supernatant decreased with increasing radiation dose. These results are consistent with widely reported radiation-mediated damage of proteins by crosslinking, a modification that reduces protein solubility. However, in preliminary studies using tissues packaged in a less hydrated environment consisting of nonadherent gauze, this radiation dose dependent decrease in protein extractability was eliminated (see Example 6).

Peptide Analysis:

Protein extractability may reflect the general biochemical state of processed tissues; more relevant parameters supporting the development of an antimicrobial wound dressing are the integrity and solubility of antimicrobial peptides. To evaluate these parameters, immunoblot analysis was performed on proteins extracted from irradiated and non-irradiated 2D2 tissues. Punch biopsies were obtained from 2D2 tissues and transferred into serum-free growth medium for an additional 48 hr. Conditioned media from duplicate tissues were collected, proteins were resolved by SDS-PAGE, transferred to PVDF membranes, and processed for immunoblot analysis using standard methods. Antimicrobial peptides were detected using hCAP18-specific antibodies, which detect the intact human antimicrobial protein hCAP18 and its bioactive proteolytic fragment, LL-37. Both intact hCAP18 and LL-37 were readily detected in media conditioned by tissues, independent of radiation dose, and the migration pattern of these proteins on SDS-PAGE was also unaffected by radiation doses utilized in these studies. There were slight increases in peptide released from non-irradiated control tissues. These slight increases may be due to new synthesis and secretion of peptide from the viable tissue, or as a result of increased peptide solubility in these tissues. Despite this observation, cathelicidin antimicrobial peptides remain intact and can be readily extracted from irradiated tissues.

Figure 5:
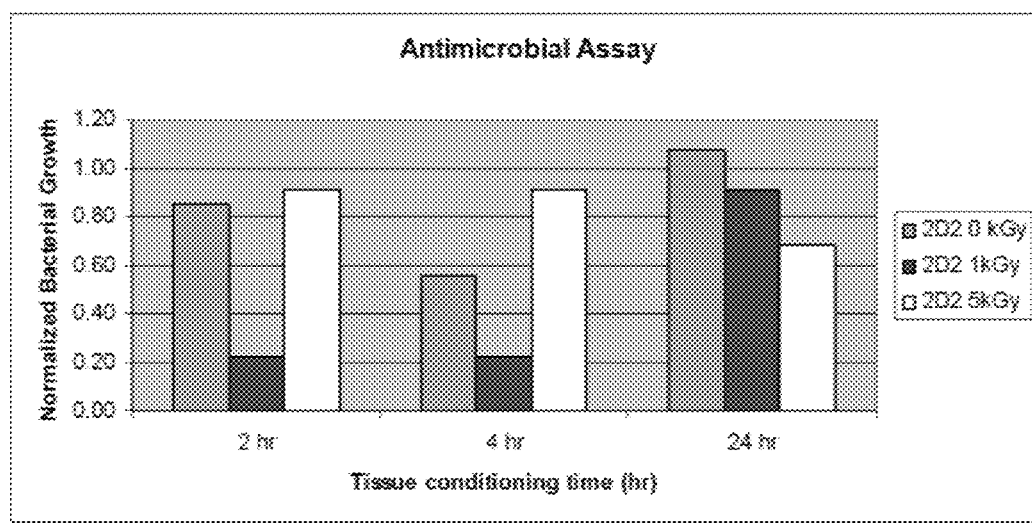
FIG. 5. Antimicrobial activity of irradiated 2D2 tissues. Punch biopsies obtained from non-irradiated and irradiated 2D2 tissues were incubated for the indicated times in serum-free culture media. Antimicrobial activity of material extracted from these tissues was determined by CFU counting and normalized against control bacterial cultures. Each data point represents average values obtained from two independent samples.

Antimicrobial Activity Assay:

Having established the integrity of released antimicrobial peptides from non-irradiated and irradiated tissues, we evaluated control and irradiated tissues for antimicrobial properties. Briefly, punch biopsies were obtained from irradiated or non-irradiated tissues, and transferred to serum-free culture medium for 2, 4, or 24 hr. to allow for extraction of antimicrobial peptides. Media were collected and combined with an inoculum of $1.0 \times 10^3$ CFU of $S.$ $carnosus$ in bacterial growth media. This mixture was incubated at 37° C. with constant shaking for 60 min. Afterward, samples were plated onto bacteriological plates using a WASP2 Spiral Plater (Microbiology International, Frederick, Md.) and incubated for 16 hr. at 37° C. Colonies were counted, and viable bacterial density, expressed in CFU/mL, was determined. Values were normalized to the density of bacterial cultures grown in the presence of serum-free growth medium without tissue extracts. As shown in FIG. 5, samples extracted from 2D2 tissues treated with 1 kGy radiation exhibited enhanced antimicrobial activity as indicated by decrease in bacterial density relative to non-irradiated tissues at conditioning periods of 2 and 4 hours. This transient increase in antimicrobial activity was not observed in tissues treated with a 5 kGy dose, nor was it evident under longer tissue conditioning times. A similar increase in activity was seen in 9F1 tissues that had been irradiated at 1 kGy (data not shown). This improved antimicrobial activity is surprising given that irradiated tissues may release lower amounts of total protein and cathelicidin antimicrobial peptides over longer time periods. However, while the above studies utilized tissues that were incubated for at least 48 hr, improved antimicrobial activity was observed only in samples extracted from irradiated tissues for 2 or 4 hr.

In total, biochemical analysis of irradiated skin equivalents revealed that the overall level of soluble protein was decreased, but antimicrobial peptide integrity was largely preserved. Peptides extracted from skin equivalent tissues irradiated at 1 kGy were shown to reduce bacterial growth by up to 80% relative to control bacterial cultures. These results demonstrate the feasibility of maintaining the biological activity of these terminally processed engineered skin tissues.

Example 5

Storage of Irradiated Skin Equivalent Tissues

An analysis of the short-term storage capabilities of irradiated 9F1 and 2D2 tissues stored on nutrient gels was undertaken. In these studies, refrigerated irradiated tissues were analyzed at 7 days and 37 days post treatment, and assessed or assayed for tissue architecture and antimicrobial peptide activities. Overall tissue organization of irradiated tissues was preserved during 37 days of refrigerated storage. At the dose levels examined, refrigerated tissues maintained both dermal and epidermal compartments. Within epidermal compartments, basal and spinous keratinocyte layers remain distinct, and cornified layers remain largely unchanged. Minimal cellular damage within the tissue manifests as intercellular spaces between keratinocytes in the basal and suprabasal layers, and storage of tissues results in partial separation between the dermal and epidermal compartments. However, this was noted in tissues at all time periods examined.

Figure 6:
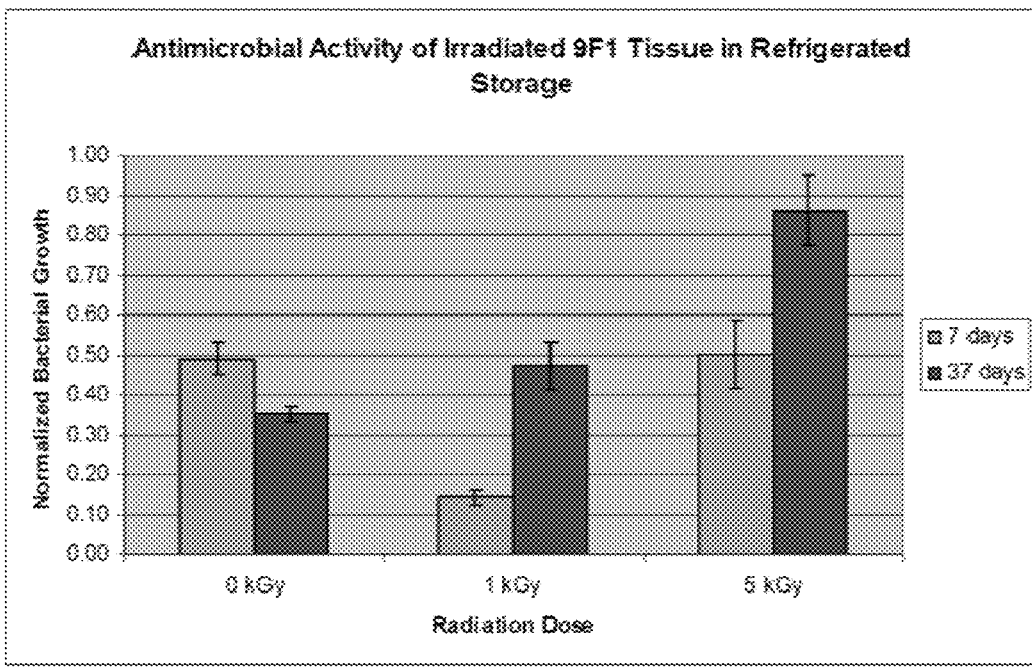
FIG. 6. Antimicrobial activity of irradiated 9F1 tissues. Punch biopsies obtained from non-irradiated and irradiated 9F1 tissues were incubated for 4 hr in serum-free culture media. Antimicrobial activity from these tissues was determined by CFU counts and normalized against control bacterial cultures, whose value was set to 1. Each data point represents average values+/−the standard deviation from four biopsy samples from tissues in the indicated treatment group.
Figure 7:
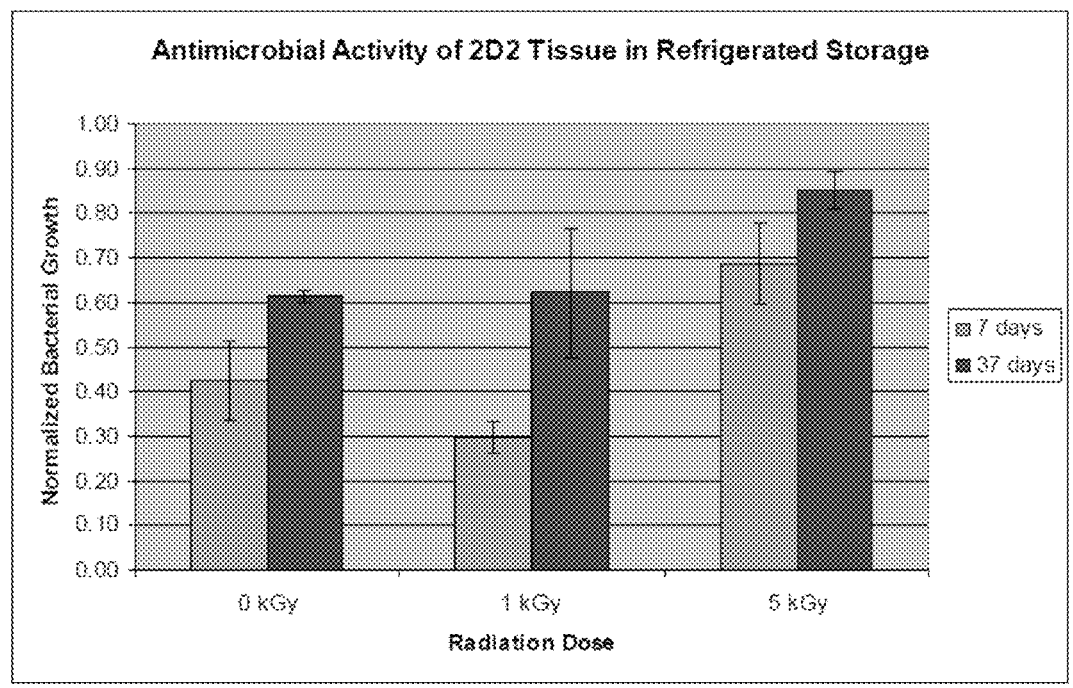
FIG. 7. Antimicrobial activity of irradiated 2D2 tissues. Punch biopsies obtained from non-irradiated and irradiated 2D2 tissues were incubated for 4 hr in serum-free culture media. Antimicrobial activity from these tissues was determined by CFU counts and normalized against control bacterial cultures, whose value was set to 1. Each data point represents average values+/−the standard deviation from four biopsy samples from tissues in the indicated treatment group.

Antimicrobial Peptide Activity:

Samples were obtained from irradiated or non-irradiated 9F1 and 2D2 tissues that had been stored at refrigerated temperatures for either 7 days or 37 days after irradiation. Antimicrobial activity assays were performed as above. Bacterial density (CFU/mL) was determined and data were normalized to bacterial cultures grown in the presence of fresh serum-free growth medium. Results of these studies are shown in FIGS. 6 and 7 for 9F1 and 2D2 tissues, respectively. 9F1 tissues, irradiated with 1 kGy radiation and stored refrigerated for 7 days, demonstrated an 86% reduction in bacterial growth relative to control bacterial cultures. In comparison, non-irradiated 9F1 tissues resulted in a 52% reduction in bacterial growth. Similarly, 1 kGy irradiated 2D2 tissues refrigerated for 7 days resulted in a 72% reduction in bacterial growth, compared to a 57% reduction caused from non-irradiated 2D2 tissues. The antimicrobial activities of 1 kGy-irradiated 9F1 and 2D2 tissues returned to approximately those of non-irradiated tissues by 37 days of refrigerated storage, but still exhibited antimicrobial activity relative to control cultures. Although all tissues treated with 5 kGy retained measurable antimicrobial activity at 7 days of post-irradiation storage, this activity was reduced upon prolonged storage. These data suggest that irradiated tissues can provide antimicrobial activity that is detectable after more than one month of refrigerated storage.

Example 6

Effects of Packaging Configuration

Tissues which had been processed in Example 2, above, were observed to detach from the underlying support membrane, resulting in folding and wrinkling of tissues. To circumvent this phenomenon, a packaging configuration was developed that prevented tissue movement. In this modified configuration, tissues were removed from their inserts, transferred onto sterile, nonadherent gauze, and sealed in sterile plastic bags. After removal from the plastic bag, tissues showed no evidence of wrinkling or folding.

Figure 8:
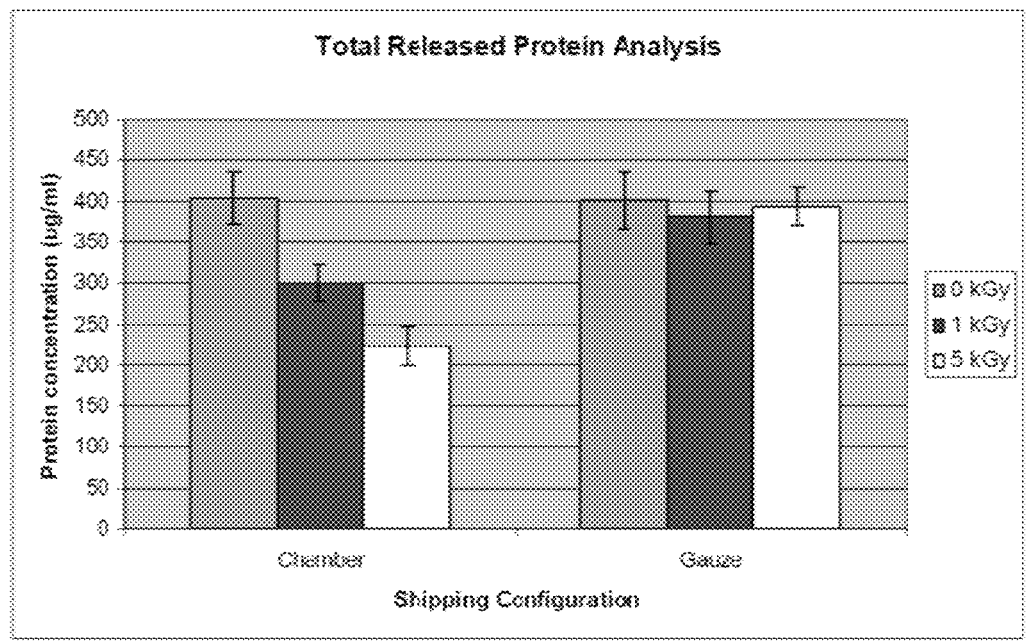
FIG. 8. Total released protein from skin equivalent tissues stored on nutrient gels or nonadherent gauze. Human skin equivalent tissues were irradiated and punch biopsies were harvested after 14 days and incubated in 0.2 ml of sterile water at 37° C. for 24 hr. Extracted protein was quantified by BCA assay. Data represent mean values+/−the standard deviation from four measurements.

The effects of gamma irradiation on proteins have been described elsewhere, and these effects are mediated in large part by free radicals and reactive oxygen species generated by hydrolysis of water molecules within the sample. Due to the high moisture content in nutrient gel chambers used for transport of the engineered tissue products, it was anticipated that irradiated tissues packaged on nutrient gel chambers or dry nonadherent gauze during irradiation treatment would exhibit different biochemical properties. Punch biopsies were obtained from non-irradiated and irradiated 2D2 and 9F1 tissues and submerged in 0.2 mL sterile water. Biopsies were incubated at 37° C. for 24 hr, supernatants were collected, and eluted proteins were quantified by BCA assay. As shown in FIG. 8, total water-soluble protein decreased with increasing radiation dose in tissues packaged on nutrient gel chambers, consistent with studies described above. In contrast, packaging of irradiated tissues on nonadherent gauze restored protein accessibility to approximately that of control levels. Packaging of tissues on gauze prior to irradiation may therefore reduce the level of protein damage in irradiated tissue by presenting an environment that is less permissive for protein crosslinking.

Example 7

Freeze Drying of Engineered Skin Equivalents

Engineered skin equivalents are manufactured as described in Example 1. Upon completion, TRANSWELL inserts containing skin equivalents are aseptically transferred into plastic TRANSWELL dishes, covered, and placed on the shelf of a VIRTIS Genesis Freeze Dryer (Gardiner, N.Y.) maintained at 20° C. Tissues are frozen by reducing the temperature from 20° C. to −20° C. at a rate of −1.33° C. per minute at 2100 mT pressure; and from −20° C. to −60° C. at a rate of −0.67° C. per minute at 2100 mT pressure. Vacuum is applied to reduce pressure to 0 mT, and tissues are warmed from −60° C. to 20° C. at +0.25° C. per minute. Drying is completed by holding samples at 0 mT at 20° C. for at least 16 hours.

Example 8

Vacuum Drying of Engineered Skin Equivalents

Engineered skin equivalents are manufactured as described in Example 1. TRANSWELL inserts containing skin equivalents are aseptically transferred into plastic TRANSWELL dishes, covered, and placed on the shelf of a VIRTIS Genesis Freeze Dryer chamber maintained at 25° C. Chamber pressure is reduced at eight minute intervals to the following: 900 mT, 830 mT, 760 mT, 690 mT, 620 mT, 550 mT, 490 mT, 430 mT, 370 mT, 310 mT, 250 mT, 200 mT, 150 mT, 100 mT, 50 mT, 25 mT. Samples are held at 25 mT for at least 16 hours to complete drying.

Example 9

Dry Mass of Engineered Skin Equivalents

Engineered skin equivalents are manufactured and wet tissue masses are obtained before and after freeze drying. Tissue mass obtained after freeze drying range from 11.7% to 13.7% of original wet tissue mass. (Table 1).

TABLE 1

| Dry mass measurement of engineered skin equivalents | | | |
|---|---|---|---|
| Tissue I.D. | Wet Mass (mg) | Dry Mass (mg) | % of Wet Mass |
| 050508-1 | 1330.2 | 156.0 | 11.7 |
| 050508-2 | 1035.5 | 122.4 | 11.8 |
| 050508-3 | 1204.4 | 165.2 | 13.7 |

Example 10

Irradiation of Dried Engineered Skin Equivalents

Skin equivalent tissues engineered for overexpression of the host defense peptide hCAP18/LL-37 are manufactured as described in Example 1, and dried as described in Examples 7 and 8. After drying, tissues are removed from TRANSWELL inserts and heat-sealed in sterile plastic bags. Dried tissues are irradiated at Sterigenics as described in Example 2, at dose levels of 1, 5, or 25 kGy, followed by storage of tissues at room temperature for up to two months. Overall tissue architecture is assessed by staining of histological sections with hematoxylin and eosin. Tissue viability is assessed by MTT assay as described in Example 2. Tissue barrier function is assessed in dried irradiated tissues using impedance meter measurements. Specimens obtained from dried, irradiated tissues are strained to failure under uniaxial tension and mechanical properties were determined. Antimicrobial peptide levels were quantified by ELISA of soluble extracts obtained from dried, irradiated tissues.

Figure 9:
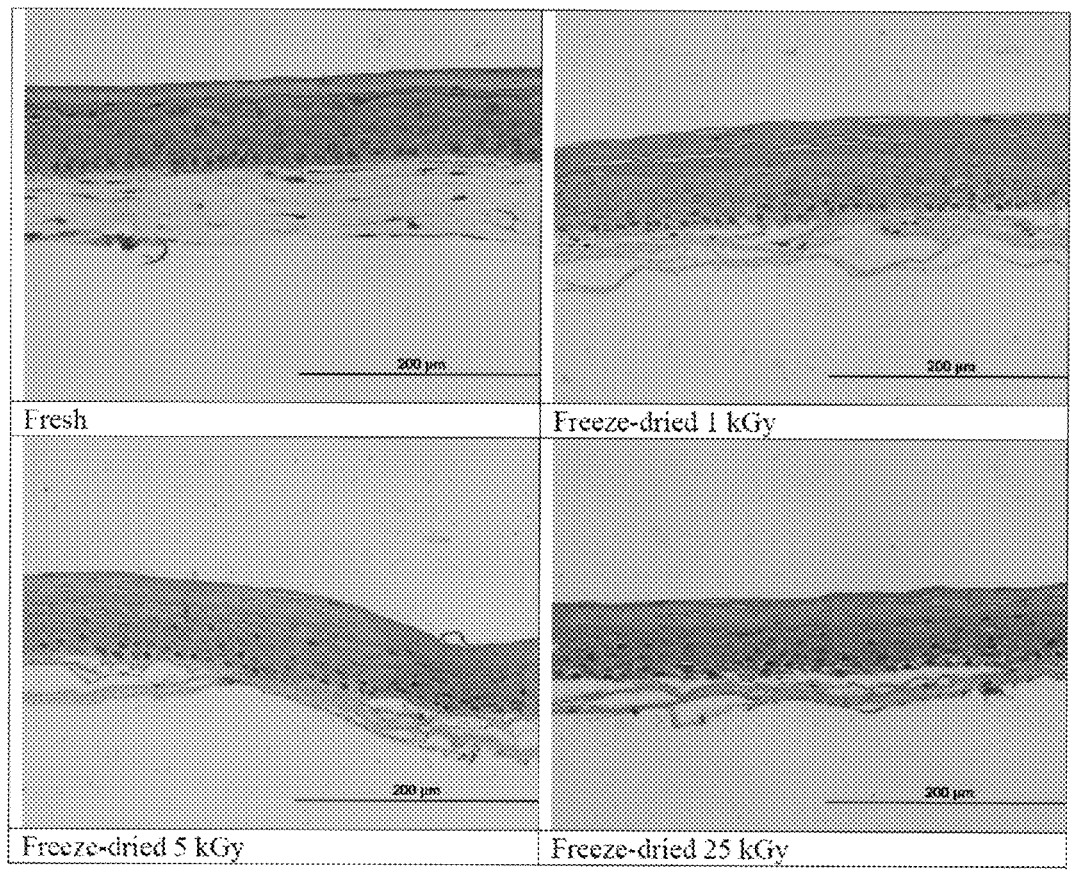
FIG. 9. Histological analysis of freeze-dried irradiated engineered skin equivalents. Fresh skin equivalents were compared to skin equivalents that were freeze-dried, or freeze-dried and irradiated at 1 kGy, 5 kGy, or 25 kGy dose level. Tissue sections were stained with hematoxylin/eosin and photographed at 400× magnification. Scale bar=200 μm FIG. 10. Histological analysis of vacuum-dried irradiated engineered skin equivalents. Fresh skin equivalents were compared to skin equivalents that were vacuum-dried, or vacuum-dried and irradiated at 1 kGy, 5 kGy, or 25 kGy dose level. Tissue sections were stained with hematoxylin/eosin and photographed at 400× magnification. Scale bar=200 μm FIG. 11. Viability of irradiated vacuum-dried and freeze-dried skin equivalents. Bar colors represent (from left to right): black=0 kGy (nonirradiated); dark gray=1 kGy; light gray=5 kGy; white=25 kGy. Data points represent the average+/−standard deviation (n=4-8), normalized to freshly prepared, nonirradiated skin equivalent tissue.
Figure 10:
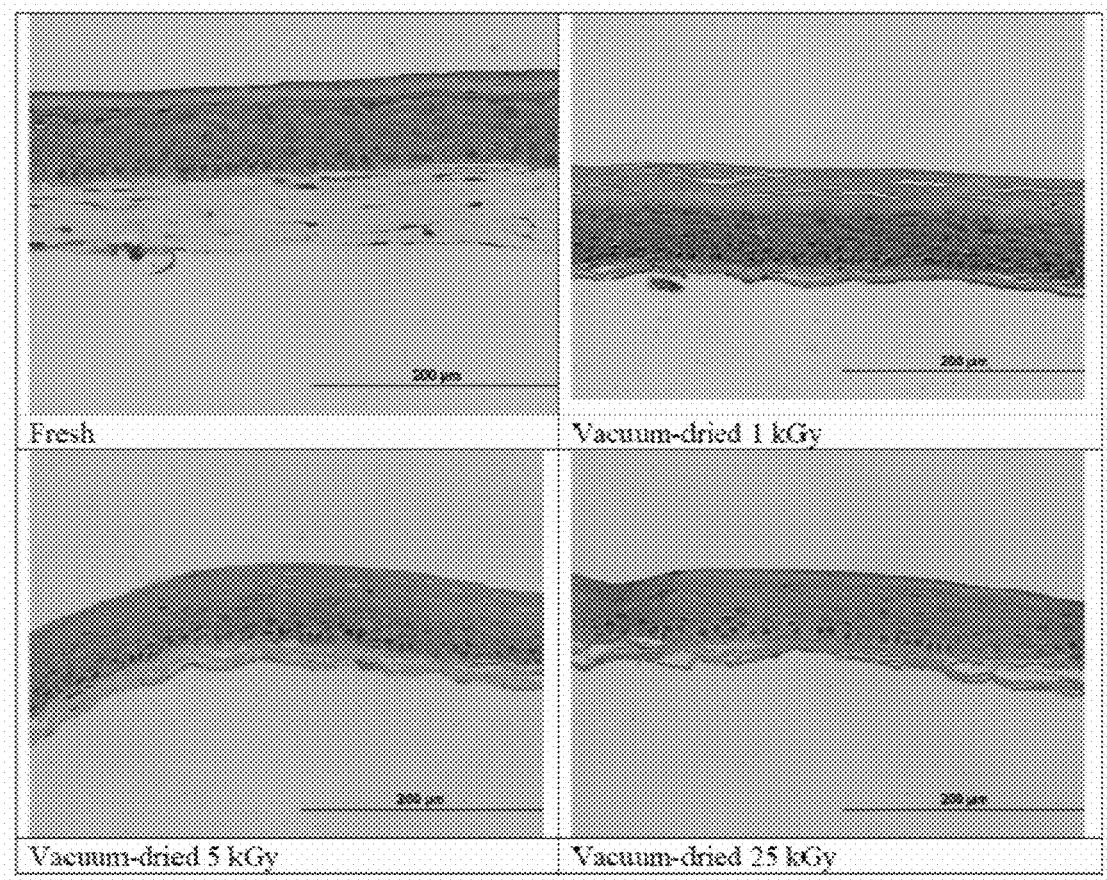

Histological Analysis:

Biopsies are obtained from fresh tissues, or from tissues that had been freeze-dried or vacuum-dried at ambient temperature and subsequently irradiated at one of three dose levels and stored at ambient temperature for up to two months. Specimens are processed for histological staining using hematoxylin/eosin in order to visualize tissue architecture, and digital micrographs are obtained at 400× magnification. Representative images of irradiated freeze-dried and vacuum-dried tissues are shown in FIG. 9 and FIG. 10, respectively. Freshly prepared specimens exhibit expected tissue architecture for engineered skin substitute tissues (FIGS. 9 and 10, panel 1).

Freeze-dried skin equivalent tissues subjected to radiation maintain normal gross tissue architecture, with recognizable dermal and epidermal components (FIG. 9). The dermal compartment exhibits structural changes, including compaction and partial delamination from the epidermal compartment. Within the epidermal compartment, organization of the basal, spinous, and stratum corneum layers are largely preserved.

Vacuum-dried irradiated engineered skin equivalents retain normal gross histology (FIG. 10); including recognizable dermis, basal and spinous keratinocyte layers, and stratum corneum. However, compaction of both the dermal compartment is evident, resulting in a tissue which is thinner than unpreserved tissues. Increases in radiation dose did not introduce further changes in the overall histology of vacuum-dried tissues.

Figure 11:
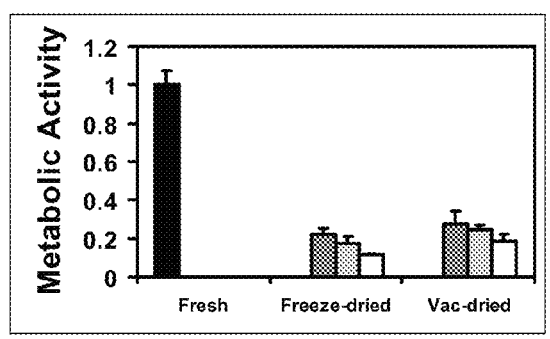

Viability Testing by MTT Viability Assay:

Punch biopsies (8 mm diameter) were harvested from fresh tissues or from tissues that had been freeze-dried or vacuum-dried at ambient temperature and irradiated at one of three doses. Biopsies were processed, and metabolic activity was quantified by measuring absorbance of the samples at 550 nm using a TECAN GENios plate reader (TECAN US, Durham, N.C.). Metabolic activity was normalized to freshly prepared control tissues. As shown in FIG. 11, metabolic activity was reduced by up to 90% using a combination of drying and irradiation, consistent with the previously observed reduction in metabolic activity observed in irradiated tissues (Example 2).

Tissue Barrier Function Analysis:

Barrier function was performed on ASTM dog-bone shaped specimens cut from engineered skin tissues that were either vacuum- or freeze-dried and exposed to one of three radiation doses (1, 5, or 25 kGy). Specimens were punched from tissues following drying and packaged individually before storage or irradiation.

Dog-bone shaped specimens were removed from their packaging, rehydrated, and tested for barrier function. Briefly, specimens were placed epidermal-side-up onto TRANSWELL inserts, placed into dishes with 10 ml of media, and allowed to rehydrate (from the bottom up) for 1 hr at room temperature. The TRANSWELL inserts were transferred to wetted filter papers and allowed to equilibrate for 45 min. Epidermal barrier function in the grip regions of each specimen was quantified by measuring the surface electrical capacitance of the tissue surface with a NOVA Dermaphase meter (NOVA Technology Corp, Portsmouth, N.H.), which is used clinically to assess epidermal barrier function. Changes in the impedance measurements over a 10 second measurement period reflect changes in the hydration state of the tissue surface. Because increased hydration results from passage of water through the stratum corneum, the magnitude of the change reflects the integrity of the epidermal permeability barrier. Based on barrier function data collected from more than 80 lots of StrataGraft® tissue, initial readings of <294 DPM and changes of less than 658 DPM units are considered acceptable barrier function.

Figure 12:
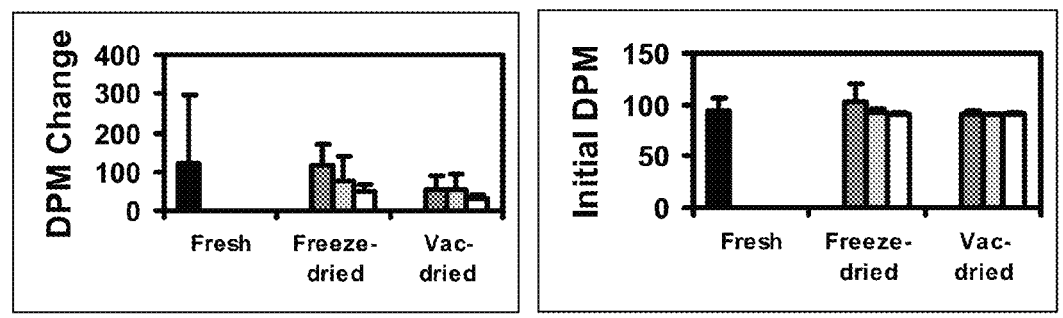
FIG. 12. Epidermal barrier function of dried irradiated skin equivalents. Left panel. The change in tissue surface electrical capacitance was measured over a 10 second interval for freeze-dried or vacuum-dried engineered skin tissues irradiated at 1 kGy, 5 kGy or 25 kGy. Values represent mean+/−standard deviation from two measurements from each of two independent tissues. Right panel. Initial DPM values are reported for freeze-dried or vacuum-dried tissues irradiated at 1 kGy, 5 kGy or 25 kGy. Bar colors represent (from left to right): black=0 kGy (nonirradiated); dark gray=1 kGy; light gray=5 kGy; white=25 kGy. Values represent mean+/−standard deviation from two measurements from each of two independent tissues.

As shown in FIG. 12, the change in tissue surface electrical impedance and initial DPM readings were similar for dried irradiated tissues and freshly prepared engineered skin tissues. Both freshly prepared and dried irradiated tissues achieved epidermal barrier function that was deemed acceptable according to the historical data compiled for StrataGraft® skin tissue. Based on these results, it is anticipated that irradiation of dried engineered skin tissue will not cause adverse effects on the barrier function of the resultant product.

Tensile Strength Analysis—

Figure 13:
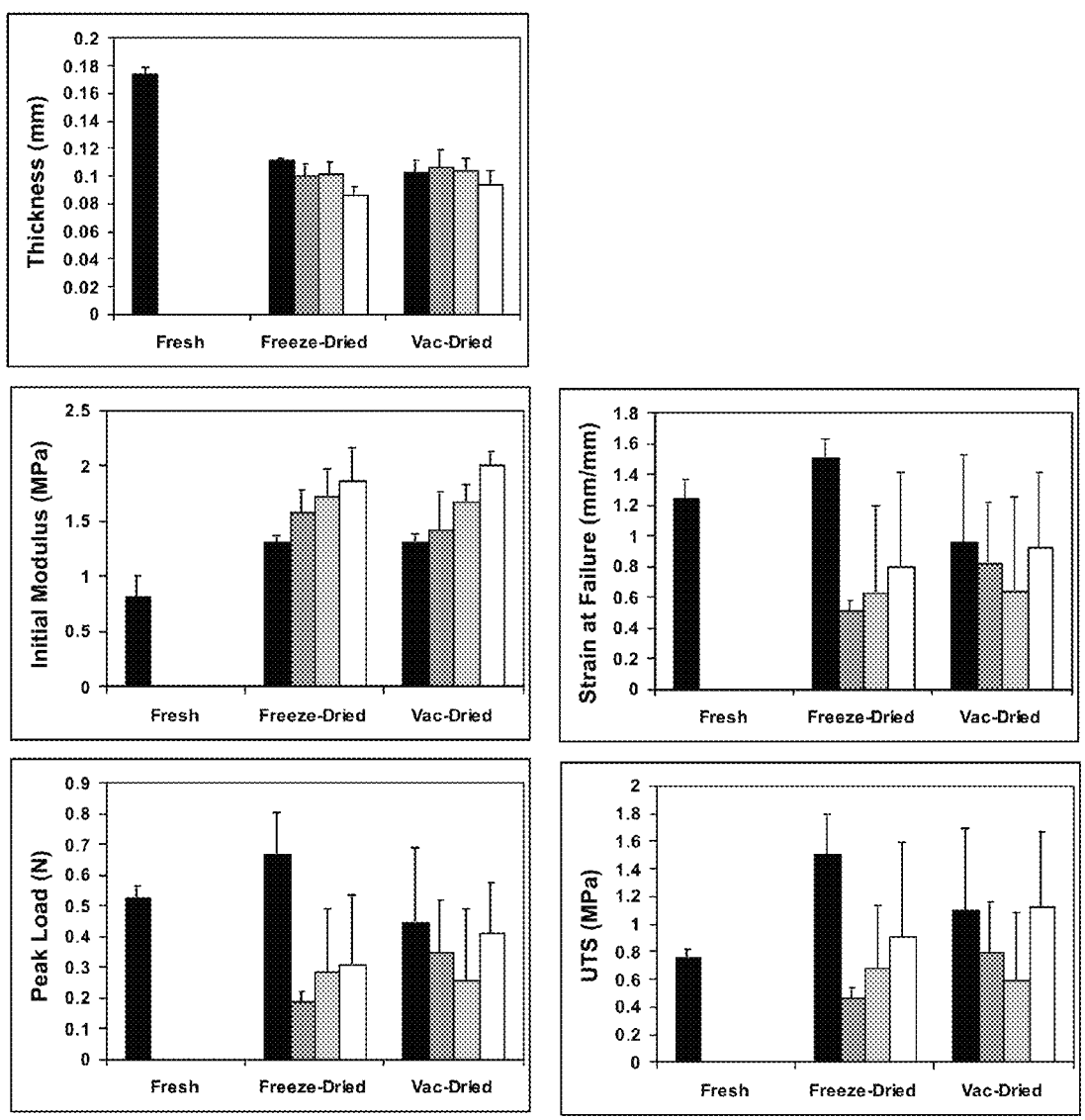
FIG. 13. Mechanical properties of dried and irradiated engineered skin tissues. Bars colors represent (from left to right): black=0 kGy (nonirradiated); dark gray=1 kGy; light gray=5 kGy; white=25 kGy. Data are mean±std. n=2-4

Following epidermal barrier testing, each specimen was submerged in 10 ml of PBS and allowed to rehydrate for at least 1 additional hour. Following rehydration, specimen thickness was measured in the gage region using a Mitutoyo thickness gauge. Tensile specimens were then pulled to failure in uniaxial tension at a rate of 100%/min (25 mm/min), with specimen hydration maintained by PBS recirculation. Load and displacement data from each experiment were exported to Microsoft Excel for analysis and data compilation. Data from these analyses are presented in FIG. 13.

Drying and irradiation of engineered skin equivalents resulted in variable effects on the mechanical properties of the tissues. Analysis of the mechanical testing results was complicated by the high variability between tissue specimens, however several strong trends were observed. Dried tissues, regardless of drying method or irradiation dose, are unable to fully regain their pre-drying thickness following rehydration, resulting in significantly thinner tissue specimens when compared to fresh controls. From histology, this reduction appears to occur mainly in the dermal layer, with epidermal thickness remaining relatively constant. There is also a strong trend for drying to result in a stiffer and more brittle tissue, with irradiation adding to this effect. This can be seen by both the increased initial modulus, as well as the reduction in elongation at failure. Although some of the increase in modulus values can be attributed to the reduction in thickness (increasing the measured stress for a given increase in load), thickness differences do not fully account for the differences between groups.

The degree of variability in the results makes it difficult to discern additional effects with statistical certainty. Average tensile strength did not appear to be adversely affected by either drying or irradiation up to 25 kGy; however, irradiation may have caused a slight, but statistically insignificant, decrease in the peak load.

Antimicrobial Peptide analysis:

hCAP18-derived peptides from engineered skin equivalents were quantified using a commercially available ELISA detection kit. Soluble extracts were prepared by topically applying serum-free culture medium to the surface of fresh or preserved tissues (0.16 ml serum-free medium per $cm^2$), and equilibrating the tissues for 2 hr. at 37° C. Extracts were used in an ELISA that detects intact hCAP18 protein and posttranslationally processed LL37 metabolites. Samples were quantified relative to a standard curve of recombinant LL37 peptide and hCAP18 protein levels were expressed as ng protein per ml of tissue extract.

As shown in Table 2, freeze-dried and vacuum-dried tissues exhibited levels of extractable hCAP18-derived peptide greater than 75% of those obtained from freshly prepared engineered skin tissues.

TABLE 2

Quantification of hCAP18-derived Peptides in Dried Irradiated engineered skin equivalents. Values are reported as mean concentration ± standard deviation of immunoreactive protein in tissue extracts from two independent tissues.

| Treatment Group | hCAP18 protein (ng/ml) |
| --- | --- |
| EG111008 Fresh | 97.4 ± 14 |
| EG111008 Freeze-dried 0kGy | 73.1 ± 4.8 |
| EG111008 Freeze-dried 1kGy | 183 ± 4.8 |
| EG111008 Freeze-dried 5kGy | 179 ± 2.0 |
| EG111008 Freeze-dried 25kGy | 120 ± 3.2 |
| EG111008 Vacuum-dried 0kGy | 122 ± 10 |
| EG111008 Vacuum-dried 1kGy | 120 ± 15 |
| EG111008 Vacuum-dried 5kGy | 77.7 ± 3.4 |
| EG111008 Vacuum-dried 25kGy | 66.8 ± 7.0 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in tissue culture, molecular biology, biochemistry, or related fields are intended to be within the scope of the following claims.

We claim:

1. A method for treating a wound in a subject comprising: applying an isolated, non-viable, in vitro human skin equivalent to said wound in said subject under conditions such that said skin equivalent contacts said wound and said wound is treated, wherein the skin equivalent comprises organotypically cultured keratinocytes that have stratified into squamous epithelia, said keratinocytes express an exogenous antimicrobial polypeptide and cell viability in the skin equivalent has been eliminated.

2. The method of claim 1, wherein said skin equivalent is applied to said wound temporarily.

3. The method of claim 1, wherein said skin equivalent is sterile.

4. The method of claim 3, wherein said sterile skin equivalent is irradiated.

5. The method of claim 1, wherein said skin equivalent is dried.

6. The method of claim 5, wherein said skin equivalent has a mass of less than 50% of the mass of a wet skin equivalent.

7. The method of claim 6, wherein said skin equivalent, after rehydration, has an initial DPM value of from 20 to 300, and a DPM change value of from 5 to 400.

8. The method of claim 6, wherein said skin equivalent, after rehydration, has a tensile strength of from 0.1 to 5.0 MPa.

9. The method of claim 1, wherein said skin equivalent comprises Near-Diploid Immortalized Keratinocytes (NIKS) cells.

10. The method of claim 1, wherein said antimicrobial polypeptide is selected from the group consisting of human beta-defensin 1, human beta-defensin 2, human beta-defensin 3, cathelicidin, and combinations thereof.

11. The method of claim 10, wherein said antimicrobial polypeptide is provided in a quantity of from 10 to 500 ng of antimicrobial polypeptide per milliliter of a surface extraction solution.

* * * * *